US00PP10672P

United States Patent [19]

Thompson

[11] Patent Number: Plant 10,672

[45] Date of Patent: Nov. 3, 1998

[54] SPATHIPHYLLUM PLANT NAMED 'AD1000'

[75] Inventor: Albert A. Thompson, Merritt Island, Fla.

[73] Assignee: Florida Tropical Foliage, Inc., Merritt Island, Fla.

[21] Appl. No.: 726,586

[22] Filed: Oct. 7, 1996

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 10,008 8/1997 Osiecki ..... Plt./88.1

*Primary Examiner*—Elizabeth C. Kemmerer

*Attorney, Agent, or Firm*—John H. Vynalek; Frank B. Robb

[57] ABSTRACT

A new and distinct cultivar of Spathiphyllum characterized particularly as to novelty by leaf morphology that has a surface textured in a corrugated manner with margins having an undulating appearance, the resulting plant having desirable characteristics sought for commercial production.

3 Drawing Sheets

BACKGROUND OF THE DISCLOSURE

This invention relates to a new and distinct plant cultivar of the Araceae family and, specifically, to a new and distinct plant cultivar of the genus of Spathiphyllum which is named Araceae Spathiphyllum 'AD1000'.

Certain plant varieties of the Araceae family are well known in the foliage plant market and among these is the 'Viscount' variety of the Spathiphyllum genus of the family. 'Viscount' is characterized by, among other things, foliage with leaf blades that have a solid green field and an inflorescence with a spathe of white tending to a pure snow white.

The plant forming the subject matter of this application was developed from a sport that appeared on a specimen of the 'Viscount' variety (unpatented) in a cultivated area near Merritt Island, Fla. A general objective of the invention has been to provide a plant of the Spathiphyllum genus which would be distinguishable from the other known plants of this genus and suitable for sale in the foliage plant marketplace.

This new plant of Spathiphyllum was asexually reproduced by tissue culture near Apopka, Fla. and such reproduction has shown this new variety to come true in successive generations. This propagation of the new plant by tissue culture in the usual controlled environment clearly discloses the continued maintenance of the characteristics described herein which distinguish this new plant from the parent plant and other related plants mainly by the foliage and, specifically, by leaf morphology that is textured in a corrugated manner with margins having an undulating appearance.

DESCRIPTION OF THE DRAWINGS

This new cultivar of Spathiphyllum is illustrated by the acompanying photographic drawings and depicts the plant by the best possible color representation using color photography.

FIG. 1 is a color photographic print of a leaf.

FIG. 2 is a color photographic print of the bloom.

FIG. 3 is a color photographic print of the plant in a pot.

BOTANICAL DESCRIPTION OF THE PLANT

All color references below are measured against The Royal Horticultural Society Colour Chart. Colors are approximate as color depends on horticultural practices such as light level and fertilizaton rate, among others.

Parentage: Sport.

*Parent.*—Spathyphyllum 'Viscount' (unpatented).

Propagation: Asexual reproduction by tissue culture.

Inflorescence

Blooming habit:

Spathe and spadix not different in appearance from parent. The spathe is borne singly on a strong, long peduncle; and is large, long and pointed, unfurling to an oval shape, opening well and not affected by adverse conditions.

*Peduncle.*—Long and slender; erect and stiff; Color — Green (139 A); entirely smooth and few in number. Pedicles — 18" to 22" in length; erect and sturdy. No variations or discoloration.

Spathe:

*Texture.*—Thin and not affected by wet or hot weather.

*Form.*—Oval; color is pure snow white (155C) with no variation or discoloration.

*Fragrance.*—Slight.

*Lasting quality on the plant.*—Very long.

Stamens:

*Anthers.*—Small and many.

*Filaments.*—Short.

Pistil:

*Styles.*—Number (200). Color — White.

Pistil:

*Stigmas.*—Number (200). Color — White.

Plant

Form: Spathyphyllum.

Growth: Medium and upright.

Foliage:

*Size.*—Large.

*Quantity.*—Abundant.

*Color.*—Green. New foliage — Upper side — Green (139 A). Under side — Green (139 A). Old foliage — Upper side — Green (139 A). Under side — Green (139 A).

*Shape.*—Oval, pointed, undulating.

*Texture.*—Upper side — Leathery and corrugated. Under side — Leathery and corrugated.

*Margin.*—Shape is oval and pointed.

Disease resistance: Good.

Stem:

*Size.*—12" to 15".

Strength: Stiff.

I claim:

1. A new and distinct Spathiphyllum plant as described and illustrated, characterized particularly as to novelty by leaf morphology that has a surface textured in a corrugated manner with margins having an undulating appearance.

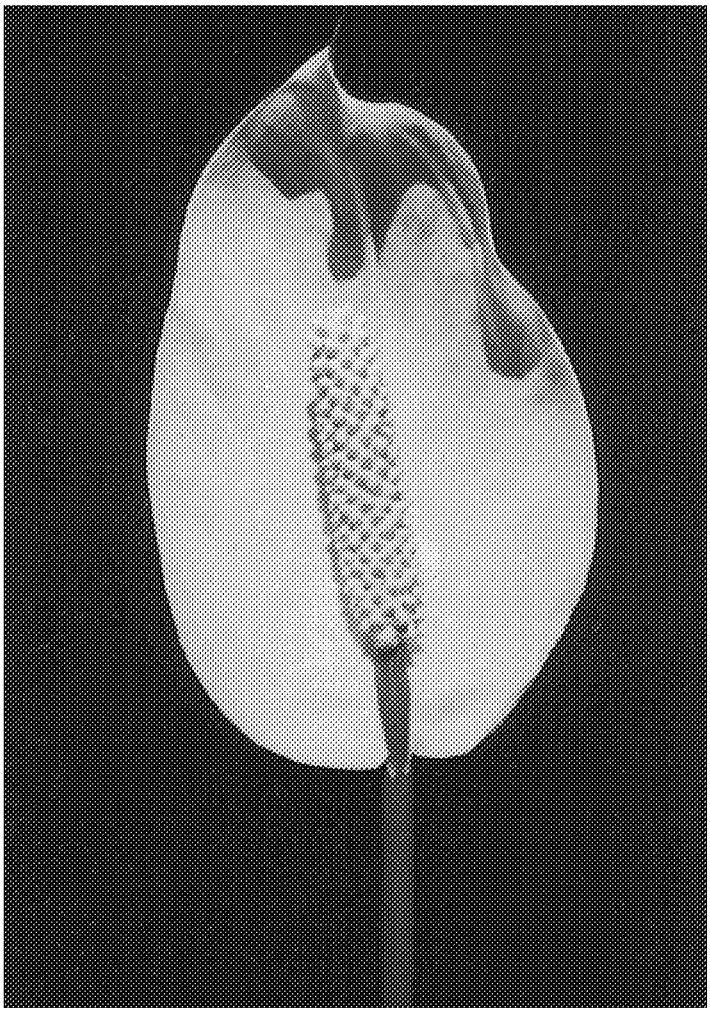

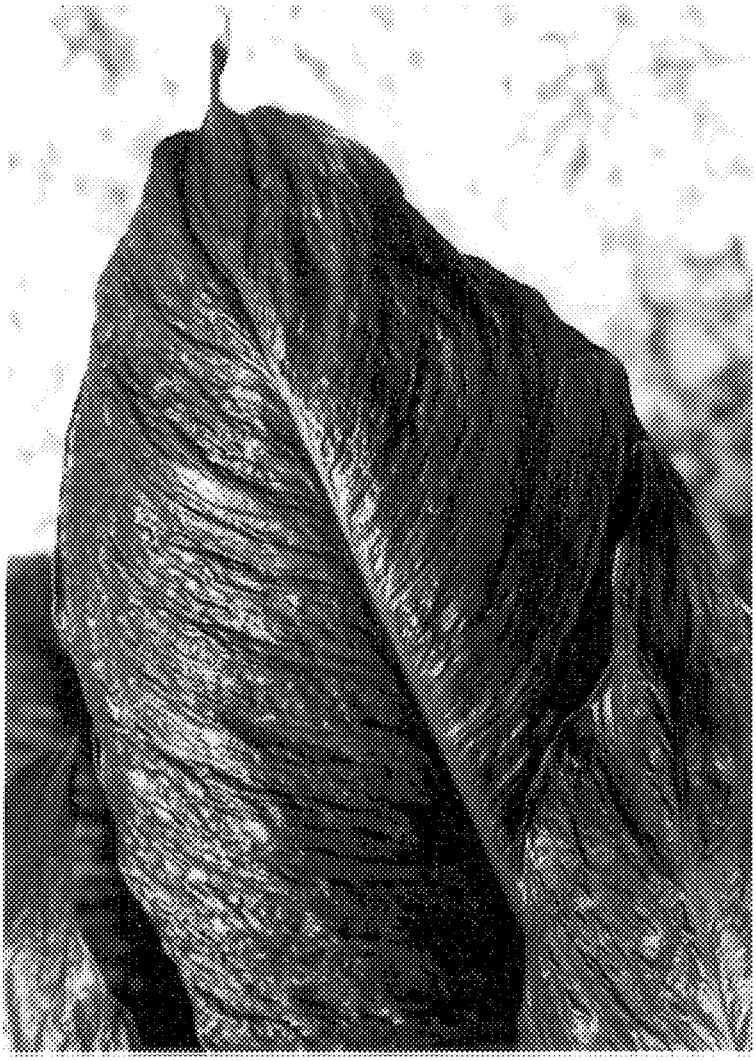

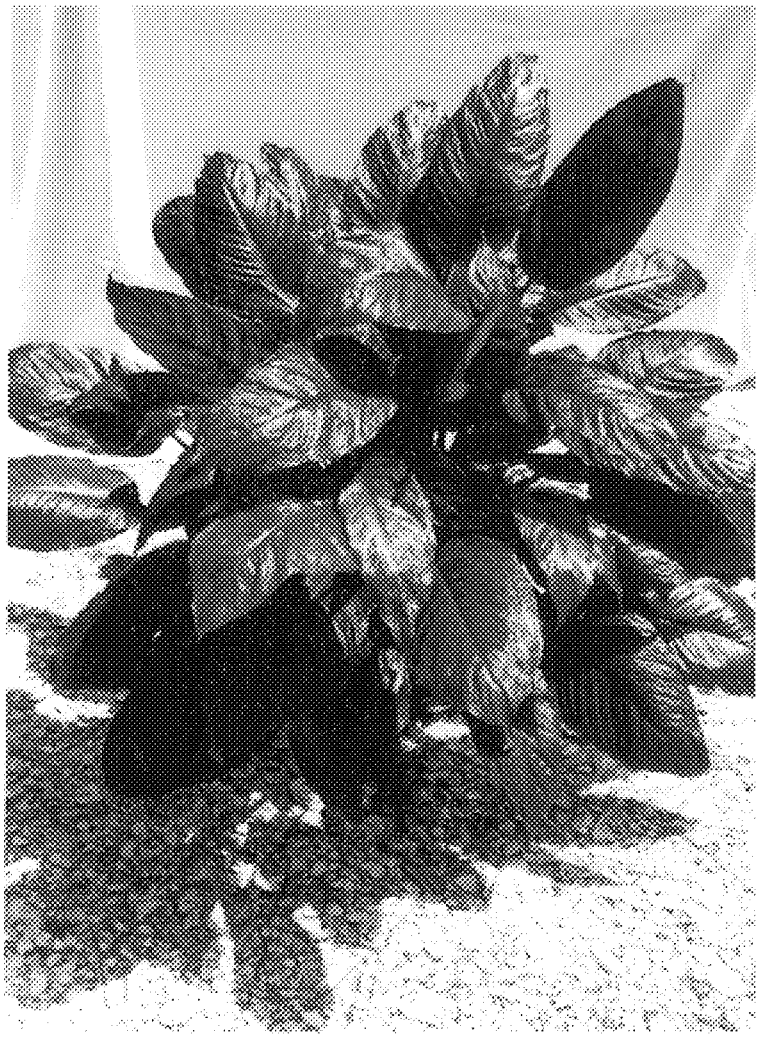

* * * * *